(12) United States Patent
Neffgen et al.

(10) Patent No.: US 9,211,236 B2
(45) Date of Patent: *Dec. 15, 2015

(54) INFILTRANT FOR DENTAL APPLICATION

(71) Applicant: ERNST MUHLBAUER GMBH & CO. KG, Norderfriedrichskoog (DE)

(72) Inventors: Stephan Neffgen, Hamburg (DE); Swen Neander, Hamburg (DE)

(73) Assignee: MUHLBAUER GMBH & CO. KG, Hamburg (DE)

( * ) Notice: Subject to any disclaimer, the term of this patent is extended or adjusted under 35 U.S.C. 154(b) by 186 days.

This patent is subject to a terminal disclaimer.

(21) Appl. No.: 13/726,348

(22) Filed: Dec. 24, 2012

(65) Prior Publication Data

US 2013/0116384 A1   May 9, 2013

Related U.S. Application Data

(63) Continuation of application No. 12/714,942, filed on Mar. 1, 2010, now Pat. No. 8,362,172.

(30) Foreign Application Priority Data

Mar. 6, 2009  (EP) .................................. 09003321

(51) Int. Cl.
 *A61K 6/08* (2006.01)
 *A61K 6/083* (2006.01)

(52) U.S. Cl.
 CPC ...................... *A61K 6/083* (2013.01)

(58) Field of Classification Search
 CPC ..................................... A61K 6/083
 USPC ................................ 526/277, 209
 See application file for complete search history.

(56) References Cited

U.S. PATENT DOCUMENTS

2003/0207960 A1* 11/2003 Jia .................................. 523/115
2010/0048761 A1*  2/2010 Ishino et al. .................. 523/116

FOREIGN PATENT DOCUMENTS

| EP | 1285947 | 5/2001 |
| EP | 1413569 | 10/2003 |
| EP | 1741419 | 6/2005 |
| EP | 1674066 | 11/2005 |
| EP | 1714633 | 4/2006 |
| EP | 1849450 | 4/2006 |
| EP | 1974712 | 3/2007 |
| EP | 2153812 | 8/2008 |
| WO | WO 02/062901 | 8/2002 |
| WO | WO 02/066535 | 8/2002 |
| WO | WO 2004/017928 | 3/2004 |
| WO | WO 2005/086911 | 9/2005 |
| WO | WO 2005/121200 | 12/2005 |
| WO | WO 2006/031972 | 3/2006 |
| WO | WO 2007/131725 | 11/2007 |

OTHER PUBLICATIONS

Buckton G, "Interfacial phenomena in drug delivery and targeting," 1997, J Controlled Release 45:207-208.
Fan, P.L. et al., Penetrativity of sealants, 1975, J. Dent. Res., 54:262-264.
Ivin, K.J., Saegusa, T., eds., "Ring-Opening Polymerization," 1984, Elsevier Appl. Sci. Publ., London, vol. 2.

\* cited by examiner

*Primary Examiner* — Ling Choi
*Assistant Examiner* — Chun-Cheng Wang
(74) *Attorney, Agent, or Firm* — Casimir Jones, S.C.

(57) ABSTRACT

The invention provides an infiltrant for dental application that comprises crosslinking monomers. In accordance with the invention the infiltrant has a penetration coefficient PC>50 cm/s, and comprises 0.05%-20% by weight of acid-group-containing monomers.

57 Claims, No Drawings

INFILTRANT FOR DENTAL APPLICATION

This application is a Continuation of U.S. application Ser. No. 12/714,942, filed Mar. 1, 2010, which is incorporated herein by reference and which claims priority to European Patent Application Number 09003321.8, filed Mar. 6, 2009.

The invention relates to an infiltrant for dental application that comprises crosslinking monomers and also to its use in treating and/or preventing carious enamel lesions.

Carious enamel lesions here are essentially instances of carious damage that extend in the dental enamel but have not yet led to cavitation (hole formation). Carious enamel lesions are demineralized regions of the dental enamel that may have a depth of up to about 2-3 mm.

The published international application WO 2007/131725A1 has disclosed treating carious enamel lesions by an infiltration method and infiltrants, to prevent cavitation and obviate the restoration with dental composites that is otherwise typically practiced. In the infiltration method, after any superficial remineralized layer present has been removed, the lesion is contacted with an infiltrant that is composed substantially of monomers, which then infiltrate. When the infiltrant has infiltrated the lesion, the monomers 30 are polymerized by means of photoactivation. This seals the lesion. The progression of the caries is halted.

Infiltration requires specific monomers or monomer mixtures, since known dental adhesion promoters, dental adhesives or dental lacquers (also known as primers, bondings or sealants) penetrate too slowly and/or inadequately into the lesion and/or infiltrate the lesion completely and/or do not cure (polymerize) completely and/or quickly. WO 2007/131725 A1 describes the use of monomers or monomer mixtures whereby the infiltrant has a penetration coefficient PC>50.

Disadvantageous features of the infiltrants described therein are their curing properties, more particularly the depth of through-cure, and also the mechanical properties of the polymerized infiltrant, more particularly the strength of the bond with the tooth substance such as, for example, the enamel, and the stress cracking stability.

The invention is based on the object of providing an infiltrant of the type specified at the outset that has improved curing properties and a good sealing effect and is also long-lived.

The infiltrant of the invention has a penetration coefficient PC>50 cm/s, and comprises 0.05%-20% by weight of acid-group-containing monomers.

First of all a number of terms used in the context of the invention will be elucidated. The term "infiltrant" refers to a liquid which as an uncured resin is able to penetrate into an enamel lesion (a porous solid). Following penetration, the infiltrant can be cured therein.

Crosslinking monomers have two or more polymerizable groups and are therefore able to crosslink polymerized chains with one another in a polymerization.

The penetration of a liquid (uncured resin) into a porous solid (enamel lesion) is described physically by the Washburn equation (equation 1, see below). In this equation it is assumed that the porous solid represents a bundle of open capillaries (Buckton G., Interfacial phenomena in drug delivery and targeting. Chur, 1995); in this case, the penetration of the liquid is driven by capillary forces.

$$d^2 = \left(\frac{\gamma \cdot \cos\theta}{2\eta}\right) r \cdot t \qquad \text{equation 1}$$

d distance by which the liquid resin moves
γ surface tension of the liquid resin (with respect to air)
θ contact angle of liquid resin (with respect to enamel)
η dynamic viscosity of the liquid resin
r capillary radius (pore radius)
t penetration time The expression in parentheses in the Washburn equation is referred to as the penetration coefficient (PC, equation 2, see below) (Fan P. L. et al., Penetrativity of sealants. J. Dent. Res., 1975, 54: 262-264). The PC is composed of the surface tension of the liquid with respect to air (γ), the cosine of the contact angle of the liquid with respect to enamel (θ), and the dynamic viscosity of the liquid (η). The greater the value of the coefficient, the faster the penetration of the liquid into a given capillary or into a given porous bed. This means that a high value of PC can be obtained through high surface tensions, low viscosities, and low contact angles, the influence of the contact angle being comparatively small.

$$PC = \left(\frac{\gamma \cdot \cos\theta}{2\eta}\right) \qquad \text{equation 2}$$

PC penetration coefficient
γ surface tension of the liquid resin (with respect to air)
θ contact angle of liquid resin (with respect to enamel)
η dynamic viscosity of the liquid resin Infiltrants are frequently applied in difficult-to-access interdental spaces (approximally). Particularly when using light-curing systems, optimum irradiation to accomplish full curing in interdental spaces is difficult. The invention has recognized that, through the use of a composition, as defined in claim 1, it is possible to achieve a sufficient depth of through-cure even under the stated difficult conditions, and also that a sufficiently high penetration coefficient can be retained, ensuring a sufficient depth of penetration of the resin. The inventive composition of the infiltrant therefore produces high penetrativity in combination with effective full curability even under the difficult conditions of approximal application.

The penetration coefficient of the infiltrant is preferably above 100 cm/s, but may also be above 150 or above 200 cm/s.

The inventively envisaged addition of acid-group-containing monomers not only increases the through-cured depth but also improves the adhesion to the tooth material such as tooth enamel, for example. Moreover, the overall amount of crosslinking monomers, especially monomers containing more than two polymerizable groups, can be lowered, leading to improved stress cracking stability. The inventive addition of the acid-group-containing monomers further enhances the durable sealing of the lesion. The barrier effect with respect to diffusion of low molecular mass nutrients, exemplified by carbohydrates (sugars), is further increased. The amount of acid-group-containing monomers is preferably 0.1% to 15%, more preferably 0.2% to 10%, more preferably 0.5% and 5%, more preferably 0.5% to 2% by weight.

Suitable acid groups are for example, carboxylic and sulfonic acid groups. Preferred acid groups in the acid-group-containing monomers are phosphoric and/or phosphonic acid groups. Examples include corresponding organic hydrogenphosphates or dihydrogenphosphates.

The acid-group-containing monomers may be of crosslinking construction—that is, may, in addition to the acid group, contain two or more polymerizable groups, examples then being monomers of the formula

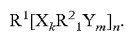

In selected applications it may be advantageous if they contain only one polymerizable group. The acid-group-containing monomers may more particularly be acrylates or methacrylates, acrylamides or methacrylamides.

For example, they may be acrylates or methacrylates which are listed later on below as preferred additional monomers having a polymerizable group, which also have a corresponding acid group.

In accordance with the invention the acid-group-containing monomers preferably have a molecular weight (weight average) of 100-1000 g/mol. The acid-group-containing monomers are preferably soluble in the nonaqueous resin mixtures of the infiltrant. The term "nonaqueous" here denotes preferably resin mixtures which contain less than 5% by weight, preferably less than 2% by weight, of water.

Acid-group-containing monomers which can be used with preference are, for example, 4-methacryloyloxyethyl-trimellitic acid (4-MET), methacryloyloxydecylmalonic acid (MAC-10), maleic acid mono-HEMA ester, N-methacryloyl-N',N'-dicarboxymethyl-1,4-diaminobenzene, N-2-hydroxy-3-methacryloyloxypropyl-N-phenylglycine, O-methacryloyltyrosinamide, 4-methacryloylaminosalicylic acid, phenyl methacryloyloxyalkylphosphates, e.g., phenyl methacryloyloxyethyl phosphate (phenyl-P), methacryloyloxyalkyl dihydrogenphosphates, e.g., methacryloyloxyethyl dihydrogenphosphate (HEMA-P), methacryloyloxypropyl dihydrogenphosphate (MPP), methacryloyloxyhexyl dihydrogenphosphate (MHP), methacryloyloxydecyl dihydrogenphosphate (MDP), glyceryl dimethacrylate phosphate (GPDM), pentaerythritol triacrylate phosphate (PENTA-P), bis(hydroxyethylmethacrylate)phosphate, (meth)acrylamidophosphates, (meth)acrylamidodiphosphates, (meth)acrylamidoalkyl phosphonates, (meth)acrylamidoalkyl diphosphonates, bismethacrylamidoalkyl dihydrogenphosphates, vinylbenzylphosphonic acid, and vinylbenzoic acid.

Among the stated methacryloyloxyalkyl dihydrogenphosphates, particular preference is given to methacryloyloxydecyl dihydrogenphosphate (MDP).

The infiltrants of the invention may be cured free-radically, anionically or cationically, depending on the chemical structure of the monomers they comprise. Preferably the monomers are curable free-radically or cationically.

The free-radical curing of the monomers of the invention can be accomplished by vinyl polymerization of suitable double bonds. Particularly suitable in this respect are (meth)acrylates, (meth)acrylamides, as disclosed in, for example, EP 1674066 A1 and EP 1974712 A1, styryl compounds, cyanoacrylates, and compounds having similarly effectively free-radically polymerizable double bonds. A further possibility of free-radical curing lies in the ring-opening polymerization of cyclic vinyl compounds such as the vinylcyclopropanes described in EP1413569, EP1741419, and EP1688125, or other cyclic systems such as vinylidene-substituted orthospiro carbonates or orthospiro esters. Another possibility also lies in the copolymerization of the ring-opening polymerizing systems with the aforementioned simply polymerizing double bonds.

Free-radical curing may also be accomplished, furthermore, by a stage reaction known under the rubric of the thiol-ene reaction, as described in WO 2005/086911.

The cationic curing of the monomers of the invention may likewise be accomplished by both ring-opening polymerization and vinyl polymerization. Suitable vinyl polymers are vinyl ethers, styryl compounds, and other compounds having electron-rich vinyl groups. Suitable ring-openingly polymerizing monomers are compounds which carry epoxide, oxetane, aziridine, oxazoline or dioxolane groups. Further ring-openingly polymerizing groups may be taken from the literature, for example: K. J. Ivin, T. Saegusa, (eds.), Vol. 2, Elsevier Appl. Sci. Publ., London 1984). Particularly suitable are silicon-containing epoxide monomers, as described in WO 02/066535 or WO 2005/121200. Particularly advantageous in the context of the use of epoxides or oxetanes is the low polymerization contraction and also the low inhibition layer of these materials.

The fraction of crosslinking monomers having two polymerizable groups can be 99.8% to 50%, preferably 99.5% to 60%, more preferably 99% to 60%, more preferably 99% to 70% by weight.

The crosslinking monomers having two polymerizable groups are preferably derivatives of acrylic and/or methacrylic acid. They may preferably be selected from the group consisting of allyl methacrylate; allyl acrylate; PRDMA, 1,3-propanediol dimethacrylate; BDMA, 1,3-butanediol dimethacrylate; BDDMA, 1,4-butanediol dimethacrylate; PDDMA, 1,5-pentanediol dimethacrylate; NPGDMA, neopentyl glycol dimethacrylate; HDDMA, 1,6-hexanediol dimethacrylate; NDDMA, 1,9-nonanediol dimethacrylate; DDDMA, 1,10-decanediol dimethacrylate; DDDDMA, 1,12-dodecanediol dimethacrylate; PRDA, 1,3-propanediol diacrylate; BDA, 1,3-butanediol diacrylate; BDDA, 1,4-butanediol diacrylate; PDDA, 1,5-pentanediol diacrylate; NPGDA, neopentyl glycol diacrylate; HDDA, 1,6-hexanediol diacrylate; NDDA, 1,9-nonanediol diacrylate; DDDA, 1,10-decanediol diacrylate; DDDDA, 1,12-dodecanediol dimethacrylate; EGDMA, ethylene glycol dimethacrylate; DEGDMA, diethylene glycol dimethacrylate; TEDMA, triethylene glycol dimethacrylate; TEGDMA, tetraethylene glycol dimethacrylate; EGDA, ethylene glycol diacrylate; DEGDA, diethylene glycol diacrylate; TEDA, triethylene glycol diacrylate; TEGDA, tetraethylene glycol diacrylate; PEG200DMA, polyethylene glycol 200 dimethacrylate; PEG300DMA, polyethylene glycol 300 dimethacrylate; PEG400DMA, polyethylene glycol 400 dimethacrylate; PEG600DMA, polyethylene glycol 600 dimethacrylate; PEG200DA, polyethylene glycol 200 diacrylate; PEG300DA, polyethylene glycol 300 diacrylate; PEG400DA, polyethylene glycol 400 diacrylate; PEG600DA, polyethylene glycol 600 diacrylate; PPGDMA, polypropylene glycol dimethacrylate; PPGDA, polypropylene glycol diacrylate; NPG(PO)2DMA, propoxylated (2) neopentyl glycol dimethacrylate; NPG(PO)2DA, propoxylated (2) neopentyl glycol diacrylate; bis-MA, bisphenol A dimethacrylate; bis-GMA, bisphenol A glycerol dimethacrylate; BPA(EO)DMA, ethoxylated bisphenol A dimethacrylate (EO=1-30); BPA(PO)DMA, propoxylated bisphenol A dimethacrylate (PO=1-30); BPA(EO)DA, ethoxylated bisphenol A diacrylate (EO=1-30); BPA(PO)DA, propoxylated bisphenol A diacrylate (PO=1-30); BPA(PO)GDA, propoxylated bisphenol A glycerol diacrylate; UDMA, diurethane dimethacrylate; TCDDMA, tricyclo[5.2.1.0]decanedimethanol dimethacrylates; TCDDA, tricyclo[5.2.1.0]-decanedimethanol diacrylates; EBA, N,N'-ethylenebisacrylamide; DHEBA, N,N'-(1,2- dihydroxyethylene)bisacrylamide; DEPBA, N,N'-diethyl(1,3-propylene)bisacrylamide; TMHMBMA, N,N'-(2,2,4-trimethylhexamethylene)bismethacrylamide; and bis[2-(2-methylacrylamino)ethoxycarbonyl]hexamethylenediamine.

The proportion of crosslinking monomers having at least three polymerizable groups can preferably be between 0% and 50%, more preferably 10% and 30% by weight.

Preferred crosslinking monomers having at least three polymerizable groups have the following formula

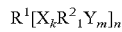

with the following definitions:

$R^1$ is a linear or branched hydrocarbon having 3-24 C atoms, comprising alkyl, cycloalkyl or aryl;

optionally containing O, N, Si, S, P as heteroatoms, examples being siloxane and/or cyclosiloxane and/or carbosilane and/or cyclocarbosilane and/or, in particular, ether groups or polyether groups, polyester groups, polysiloxane groups or polycarbosilane groups;

optionally substituted by hydroxyl and/or carbonyl and/or halogen (preferably fluorine) and/or ammonium-alkylene groups and/or siloxane and/or cyclosiloxane and/or carbosilane and/or cyclocarbosilane;

$R^2$ is a linear or branched hydrocarbon having 1-16 C atoms, comprising alkyl, cycloalkyl or aryl;

optionally containing O, N, Si, S, P as heteroatoms, examples being siloxane and/or cyclosiloxane and/or carbosilane and/or cyclocarbosilane and/or, in particular, ether groups or polyether groups, polyester groups, polysiloxane groups or polycarbosilane groups;

optionally substituted by hydroxyl and/or carbonyl and/or halogen (preferably fluorine) and/or ammonium-alkylene groups and/or siloxane and/or cyclosiloxane and/or carbosilane and/or cyclocarbosilane;

X is a linking group identically or differently selected from an ether group, carbonyl group, ester group, amide group, urethane group or urea group;

Y is a group identically or differently comprising a polymerizable double bond and/or a ring-openingly polymerizable group and/or a thiol group and/or an epoxide group and/or a vinyl, preferably (meth)acrylate and/or (meth)acrylamide;

k is 0 or 1;

l is 0 or 1;

m is at least 1;

n is at least 1; and m×n is at least 3.

It may be of advantage if the monomers have additional functional groups such as ammonium-alkylene groups or halogen, especially fluorinated alkylene.

Suitable low-viscosity monomers having at least three polymerizable groups are, for example, glycerol triacrylate, TMPTMA, trimethylolpropane trimethacrylate; TMPTA, trimethylolpropane tri(meth)acrylate; DTMPTA, ditrimethylolpropane tetra(meth)acrylate; diPENTA, dipentaerythritol penta(meth)acrylate; or DPEHA, dipentaerythritol hexa(meth)acrylate.

Preferred low-viscosity monomers having at least three polymerizable groups are based for example on alkoxylated multiple alcohols (tri-, tetra-, penta-, hexa-, polyols) such as trimethylolpropane, ditrimethylolpropane, glycerol, pentaerythritol or dipentaerythritol.

Particularly preferred are (meth)acrylic esters of alkoxylated multiple alcohols such as, for example, ethoxylated glycerol triacrylate, propoxylated glycerol triacrylate, ethoxylated trimethylolpropane trimethacrylate, ethoxylated trimethylolpropane triacrylate, propoxylated trimethylolpropane trimethacrylate, propoxylated trimethylolpropane triacrylate, ethoxylated pentaerythritol trimethacrylate, ethoxylated pentaerythritol triacrylate, ethoxylated pentaerythritol tetramethacrylate, ethoxylated pentaerythritol tetraacrylate, ethoxylated dipentaerythritol trimethacrylate, ethoxylated dipentaerythritol tetramethacrylate, ethoxylated dipentaerythritol pentamethacrylate, ethoxylated dipentaerythritol hexamethacrylate, ethoxylated dipentaerythritol triacrylate, ethoxylated dipentaerythritol tetraacrylate, ethoxylated dipentaerythritol pentaacrylate, ethoxylated dipentaerythritol hexaacrylate, propoxylated pentaerythritol trimethacrylate, propoxylated pentaerythritol triacrylate, propoxylated pentaerythritol tetramethacrylate, propoxylated pentaerythritol tetraacrylate, propoxylated dipentaerythritol trimethacrylate, propoxylated dipentaerythritol tetramethacrylate, propoxylated dipentaerythritol pentamethacrylate, propoxylated dipentaerythritol hexamethacrylate, propoxylated dipentaerythritol triacrylate, propoxylated dipentaerythritol tetraacrylate, propoxylated dipentaerythritol pentaacrylate and propoxylated dipentaerythritol hexaacrylate.

Those alkoxy groups attached to the alcohols represent (molecular-)chain extenders. Chain extension may be achieved preferably through ethoxylation or propoxylation. For chain extension there are further linking possibilities available, examples being ether bonds, ester bonds, amide bonds, urethane bonds, and the like, which may be followed in turn preferably by ethylene glycol groups or propylene glycol groups.

Preferred chain extenders are for example

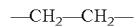

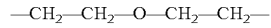

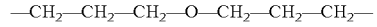

and so on

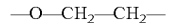

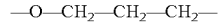

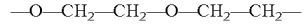

and so on

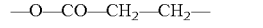

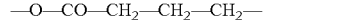

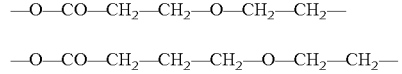

and so on

and so on

—NR³—CO—CH₂—CH₂—

—NR³—CO—CH₂—CH₂—CH₂—

—NR³—CO—CH₂—CH₂—O—CH₂—CH₂—

—NR³—CO—CH₂—CH₂—CH₂—O—CH₂—CH₂—CH₂— and so on

—O—CO—NR³—CH₂—CH₂—

—O—CO—NR³—CH₂—CH₂—CH₂—

—O—CO—NR³—CH₂—CH₂—O—CH₂—CH₂—

—O—CO—NR³—CH₂—CH₂—CH₂—O—CH₂—CH₂—CH₂— and so on

—NR³—CO—O—CH₂—CH₂—

—NR³—CO—O—CH₂—CH₂—CH₂—

—NR³—CO—O—CH₂—CH₂O—CH₂—CH₂—

—NR³—CO—O—CH₂—CH₂—CH₂—O—CH₂—CH₂—CH₂— and so on

—NR³—CO—NR³—CH₂—CH₂—

—NR³—CO—NR³—CH₂—CH₂—CH₂—

—NR³—CO—NR³—CH₂—CH₂—O—CH₂—CH₂—

—NR³—CO—NR³—CH₂—CH₂—CH₂—O—CH₂—CH₂—CH₂— and so on
where R³ is H or an alkyl group, preferably a methyl group.

The chain-extending group is functionalized preferably terminally with the crosslinking groups, preferably with a methacrylate or an acrylate group, a methacrylamide or acrylamide group.

A crosslinking point is regarded as being the position of the crosslinking polymerizable group—for example, the position of a C=C double bond in the monomer.

The chain length is preferably such that the distance between crosslinking points is at least 7, preferably at least 9, more preferably 10 to 30, with particular preference 11 to 21 bond lengths. The distance is preferably less than 50 bond lengths.

By distance between crosslinking points is meant the shortest distance between the crosslinking groups, as for example two C=C double bonds, along the molecule. The reference is therefore only to the constitution of the molecule, and not, say, to the actual spatial position of the groups relative to one another, as governed, for instance, by configuration or conformation.

By bond length is meant the distance between two atoms in the molecule, irrespective of the nature of the covalent bonding and of the exact length of the individual covalent bond.

The fraction of crosslinking monomers having at least three polymerizable groups and a distance between crosslinking points of less than 10 bond lengths, based on the total mass of the monomers, is preferably less than 20% by weight, more preferably less than 10% by weight, more preferably less than 5% by weight.

By setting a distance between the crosslinking groups, as defined above, and, consequently, by setting a corresponding network arc length in crosslinked polymers, the stresses in the cured polymer can be reduced. This reduction in stresses means that, even under temperature fluctuation loads such as, for example, thermal cycling between 5 and 55° C., which is used as a test method, there are no instances of stress-induced cracking in the polymer. The mechanical properties and especially the long-term stability of the cured infiltrant are improved in this way.

The preferred fraction of these monomers is dependent on the number of crosslinking groups in the monomer mixture, on the size of the chain-extending groups, and on the resultant PC.

The infiltrant of the invention may further comprise monomers having one polymerizable group. These monomers may preferably be selected from the group consisting of MMA, methyl methacrylate; EMA, ethyl methacrylate; n-BMA, n-butyl methacrylate; IBMA, isobutyl methacrylate, t-BMA, tert-butyl methacrylate; EHMA, 2-ethylhexyl methacrylate, LMA, lauryl methacrylate; TDMA, tridecyl methacrylate; SMA, stearyl methacrylate; CHMA, cyclohexyl methacrylate; BZMA, benzyl methacrylate, IBXMA, isobornyl methacrylates; HEMA, 2-hydroxyethyl methacrylate; HPMA, 2-hydroxypropyl methacrylate; DMMA, dimethylaminoethyl methacrylate; DEMA, diethylaminoethyl methacrylate; GMA, glycidyl methacrylate; THFMA, tetrahydrofurfuryl methacrylate; AMA, allyl methacrylate; ETMA, ethoxyethyl methacrylate; 3FM, trifluoroethyl methacrylate; 8FM, octafluoropentyl methacrylate; AIB, isobutyl acrylate; TBA, tert-butyl acrylate; LA, lauryl acryate; CEA, cetyl acrylate; STA, stearyl acrylate; CHA, cyclohexyl acrylate; BZA, benzyl acrylate; IBXA, isobornyl acrylate; 2-MTA, 2-methoxyethyl acrylate; ETA, 2-ethoxyethyl acrylate; EETA, ethoxyethoxyethyl acrylate; PEA, 2-phenoxyethyl acrylate; THFA, tetrahydrofurfuryl acrylate; HEA, 2-hydroxyethyl acrylate; HPA, 2-hydroxypropyl acrylate; 4HBA, 4-hydroxybutyl acrylate; DMA, dimethylaminoethyl acrylate; 3F, trifluoroethyl acrylate; 17F, heptadecafluorodecyl acrylate, 2-PEA, 2-phenoxyethyl acrylate; TBCH, 4-tert-butylcyclohexyl acrylate; DCPA, dihydrodicyclopentadienyl acrylate; EHA, 2-ethylhexyl acrylate; and 3EGMA, triethylene glycol monomethacrylate.

The monomers, monomer mixtures and/or infiltrants preferably have a dynamic viscosity of less than 50 mPas, more preferably less than 30 mPas, with particular preference less than 20 mPas.

The mixing of different monomers serves in particular to fine-tune the mechanical properties such as hardness and strength, the depth of through-cure and/or the degree of polymerization, the residual monomer content, the extent of the lubricating layer, the contraction, the stability, the water absorption, and, in particular, the freedom from stress with retention of a high penetrativity (PC>50).

Also important in particular is the water compatibility of the monomers, in the case, for instance, where the enamel lesion still contains residual moisture after preparation (etching, rinsing, drying). Certain monomers may absorb residual moisture and so further improve penetration. Suitability for this purpose is possessed in particular by water-soluble and/or phase-mediating esters of (meth)acrylic acid, e.g., HEMA, 2-hydroxyethyl methacrylate, or GDMA, glycerol dimethacrylate, or GMA, glycerol monomethacrylate.

Mixing with further monomers may also serve in particular to fine-tune other advantageous properties such as high surface smoothness (plaque-preventing), fluoride release, X-ray opacity, adhesion to enamel, long-term color stability, biocompatibility, and so on.

The infiltrant may also comprise hyperbranched monomer's, dendrimers for example, that are familiar in the dental sector and are known to the skilled worker from, for example, WO 02/062901, WO 2006/031972 or EP 1714633, especially in order to lower the residual monomer content and to enhance the biocompatibility.

The infiltrant may comprise bactericidal monomers that are customary in the dental sector and are known to the skilled worker from, for example, EP 1285947 or EP 1849450.

The monomer mixtures and the infiltrant have a PC>50, preferably >100, more preferably >200.

The infiltrant comprises agents for curing the infiltrant. The agent for curing may be initiators that are customary in the dental sector and are known to the skilled worker, more particularly light-activated initiator systems, or else may be chemically activating initiators, or mixtures of the different systems.

The initiators that can be used here may be, for example, photoinitiators. These are characterized in that they are able, through absorption of light in the wavelength range from 300 nm to 700 nm, preferably from 350 nm to 600 nm, and more preferably from 380 nm to 500 nm, and, optionally, through additional reaction with one or more coinitiators, to effect curing of the material. Preference is given here to using phosphine oxides, benzoin ethers, benzil ketals, acetophenones, benzophenones, thioxanthones, bisimidazoles, metallocenes, fluorones, α-dicarbonyl compounds, aryldiazonium salts, arylsulphonium salts, aryliodonium salts, ferrocenium salts, phenylphosphonium salts or a mixture of these compounds.

Particular preference is given to using diphenyl-2,4,6-trimethylbenzoylphosphine oxide, benzoin, benzoin alkyl ethers, benzil dialkyl ketals, α-hydroxyacetophenone, dialkoxyacetophenones, α-aminoacetophenones, isopropylthioxanthone, camphorquinone, phenylpropanedione, 5,7-diiodo-3-butoxy-6-fluorone, (eta-6-cumene) (eta-5-cyclopentadienyl)iron hexafluorophosphate, (eta-6-cumene)(eta-5-cyclopentadienyl)iron tetrafluoroborate, (eta-6-cumene) (eta-5-cyclopentadienyl)iron hexafluoroantimonate, substituted diaryliodonium salts, triarylsulphonium salts or a mixture of these compounds.

Coinitiators used for photochemical curing are preferably tertiary amines, borates, organic phosphites, diaryliodonium compounds, thioxanthones, xanthenes, fluorenes, fluorones, α-dicarbonyl compounds, fused polyaromatics or a mixture of these compounds. Particular preference is given to using N,N-dimethyl-p-toluolidine, N,N-dialkylalkylanilines, N,N-dihyhdroxyethyl-p-toluidine, 2-ethylhexyl p-(dimethylamino)benzoate, butyrylcholine triphenylbutylborate, N,N-dimethyl-4-tert-butylaniline, N,N-diethyl-3,5-di-tert-butylaniline, 4-tert-butylaniline or a mixture of these compounds.

To 100 parts of resin or resin mixture it is preferred to add 0.05 to 2 parts of photoinitiator, more preferably 0.1 to 1 part. The coinitiator is present in excess, 1-5 times, preferably 1-3 times, relative to the initiator.

The infiltrant can be prepared from a kit having at least two components. Infiltrants comprising two components have the advantage that they can be formulated so as to be self-curing (chemical curing). In one embodiment a first component comprises monomers and chemically activable initiators and a second component comprises suitable activators.

For chemical curing at room temperature it is general practice to use a redox initiator system composed of one or more initiators and one or more coinitiators with activator function. For reasons of storage stability, initiator and/or initiators and coinitiator and/or coinitiators are incorporated into parts of the infiltrant of the invention that are spatially separate from one another, i.e., the material is a multicomponent material, preferably a two-component material. Initiator or initiators used are preferably inorganic and/or organic peroxides, inorganic and/or organic hydroperoxides, barbituric acid derivatives, malonylsulphamides, protic acids, Lewis or Broensted acids and/or compounds which release such acids, carbenium ion donors such as methyl triflate or triethyl perchlorate, for example, or a mixture, of these compounds, and coinitiator or coinitiators used are preferably tertiary amines, heavy metal compounds, more particularly compounds of groups 8 and 9 of the Periodic Table ("iron group and copper group"), compounds having ionogenically bonded halogens or pseudohalogens, such as quaternary ammonium halides, for example, weak Broensted acids such as, for example, alcohols and water or a mixture of these compounds.

In one particularly simple embodiment the instrument for applying the infiltrant (application aid) to the tooth is coated or impregnated with the activator.

In a further embodiment a first component comprises monomers and as initiators, salts of CH-acidic compounds such as barbituric acid derivatives, and a second component comprises monomers and an activating component, preferably a more strongly acidic acid than the CH-acidic compound.

In one particularly simple embodiment an instrument for applying the infiltrant (application aid) to the tooth comprises canulas containing a mixing chamber and/or mixing elements.

The infiltrant may comprise stabilizers. Preference is given to UV stabilizers. Suitable UV stabilizers are known to the skilled worker; cited here by way of example are Chimasorb® and Tinuvin® (Ciba).

The infiltrant may comprise (nonpolymerizable) solvents. Preference is given to solvents of medium volatility, such as, for example, alcohols, relatively high molecular weight ketones and ethers, and also esters, and so on. Particular preference is given to alcohols, more particularly ethanol, or to solvents having similar evaporation characteristics.

The infiltrant preferably contains less than approximately 20% by mass, more preferably less than approximately 10% by mass, with particular preference no solvent.

The infiltrant may comprise at least one fluorescent dye and/or color pigments, in order to improve the appearance and/or adapt it to the dental enamel. Suitable fluorescent colorants are known to the skilled person and described in US 2004/017928 A1, for example. The infiltrant may comprise other colorants, especially for the production of different tooth colors. The infiltrant may comprise color-changing dyes which indicate the infiltrated lesion and change color to indicate the curing of the infiltrant. Preferably the dye becomes colorless after the infiltrant is cured. The dye may be free-radically reactive.

The color change may also be dependent on other influences, such as on the pH, for example.

The dye may have adsorptive properties, particularly with respect to the dental enamel, and so accumulates in the upper layer of the lesion. In that case it is also possible to see the color change mere readily in the interdental region.

The dye may have nonadsorptive properties and may penetrate deeply into the lesion, thereby making it possible, for example, to monitor the infiltration more effectively.

The infiltrant may comprise thermochromic and/or photochromic additives which indicate the infiltrated region on irradiation with corresponding light and/or on temperature change.

The infiltrant may comprise contrast agents for the purpose of X-ray-opacity, preferably organic compounds, as disclosed in European Patent Application EP 08014437.

The invention further provides for the use of an infiltrant of the invention to treat and/or prevent carious enamel lesions. Such use may encompass the following steps:
1. removing a thin surface layer of the enamel lesion by etching agent.
2. rinsing off the etching agent
3. drying the lesion with a drying agent
4. infiltrating the lesion with an infiltrant
5. removing excesses (optional)
6. curing the infiltrant
7. infiltrating the lesion with an infiltrant (optional)
8. removing excesses (optional)
9. curing the infiltrant (optional)
10. polishing the infiltrated lesion surface (optional).

In individual steps of the infiltration method the desired result may be improved further by application of sound and/or ultrasound.

Preferred etching agents are gels of strong acids such as hydrochloric acid.

Preferred drying agents are toxicologically unobjectionable solvents with a high vapor pressure. Particular preference is given to drying agents having a vapor pressure which is greater than that of water (23 mbar [20° C.]). They are selected, for example, from alcohols, ketones, ethers, esters, etc. Particular preference is given to ethanol.

The drying agent may comprise constituents of the initiator system which remain in the lesion after the system has evaporated.

The drying agent may comprise a film-former.

The invention additionally encompasses a kit for implementing the infiltration method. Said kit comprises
1. etching agent
2. drying agent (optional)
3. infiltrant The invention is illustrated below with reference to a number of examples.

Monomer mixtures were prepared and investigations were carried out into their penetration coefficient (PC), through-cure depth, mechanical behavior, and adhesive strength (shear bond strength).

The following components were employed:

| | |
|---|---|
| TEDMA | triethylene glycol dimethacrylate |
| E3TMPTA | trimethylolpropane ethoxylated with on average 1 EO unit per methylol group and termially acrylated |
| MDP | 10-methacryloyloxydecyl dihydrogenphosphate |
| CQ | camphorquinone |
| EHA | ethylhexyl p-N,N-dimethylaminobenzoate |
| BHT | 2,6-di-tert-butylphenol |

Test Methods
Surface Tension

The surface tension of the resins was carried out by means of contour analysis on a hanging droplet (DSA 10, KRÜSS GmbH). The surface tension was measured on newly formed droplets over a time of 30 s, with one value being recorded about, every 5 s. For this purpose the resins were delivered using a fine syringe and the droplet that formed was filmed with a digital camera. The surface tension was determined from the characteristic shape and size of the droplet in accordance with the Young-Laplace equation. For each resin, 3 measurements were carried out in this way, and their average was reported as the surface tension.

Contact Angle

Each individual measurement was carried out using enamel from bovine teeth. For this purpose, bovine teeth were embedded in a synthetic resin and the enamel surface was wet-polished using a sanding machine (Struers GmbH) with abrasive papers (80, 500 and 1200 grades), thereby providing planar enamel surfaces approximately 0.5×1.0 cm in size for the contact angle measurements. Up until the time of measurement, the enamel samples were stored in distilled water, and prior to measurement they were dried with ethanol and compressed air.

The contact angle was measured using a video contact angle measuring instrument (DSA 10, KRÜSS GmbH). In this case a drop of the resin mixture was applied to the enamel surface using a microliter syringe, and within a period of 10 s up to 40 individual pictures of the droplet were taken, under computer control, and the contact angle was determined by means of droplet contour analysis software.

Through-Cure Depth

The through-cure depths of the resins were determined in accordance with the "polymerization depth" test of ISO 4049: 2000. For this purpose the resins were placed in cylindrical Teflon moulds (5 mm in diameter, 10 mm high) and exposed from above using a halogen lamp (Translux EC from Heraeus Kulzer GmbH) for 15 or 20 s. Immediately after light exposure, the cured specimens were demoulded and were freed from uncured material using a plastic spatula. The height of the cured cylindrical cone was reported as the through-cure depth (TCD).

Dynamic Viscosity

The viscosity of the resins was measured at 23° C. using a dynamic plate/plate viscometer (Dynamic Stress Rheometer, Rheometric Scientific Inc.). Measurement took place in steady stress sweep mode with slot sizes of 0.1 to 0.5 mm in the range from 0 to 50 Pa shearing stress without preliminary shearing of the resins.

Shear Bond Strength (SBS) Measurements

The adhesion of the infiltrants of the invention was measured by carrying out shear bond strength (SBS) tests. For this purpose, bovine incisors with their pulp removed beforehand, which had undergone subsequent storage in 0.5% by weight Chloramin-T solution in water, were subjected to wet planar grinding on the facing side. Depending on the conditions of the test, the planar enameled surfaces were microabraded using 15% strength HCl gel by exposure for 2 minutes, or left untreated. Then the infiltrants of the invention or the reference examples were applied to the etched enamel surface using a Mirobrush, and left to act for 240 s. Subsequently the infiltrated area was exposed for 40 s using a halogen lamp [Translux EC, from Heraeus Kulzer]. A two-piece Teflon mold with a cavity of 3.0 mm in diameter was mounted, and the photo-curing dental composite EcuSphere Shape (ultrafine glass hybrid composite; DMG) was introduced and exposed for 40 s with a halogen lamp [Translux EC, from Heraeus Kulzer]. The Teflon mold was removed and the adhesive bond was stored in water first for 23 h at 37° C. and then for 1 h at 23° C. The bond was subsequently clamped into a mount for measuring the SBS, and was subjected to measurement in an apparatus for determining a force-displacement diagram (Z010, Zwick GmbH, Ulm) at a rate of advance of 0.5 mm/min in accordance with ISO/TS 11405:2003 "Dental materials—Testing of adhesion to tooth structure". The results were recorded in the form of an average, a standard deviation (expression in brackets), and the sum of the individual measurements (n=6-8).

Description of the preparation of examples and reference examples.

The resins as per table 1 were prepared by stirring of the corresponding components together. For the investigations of through-cure depth, and adhesive strength (shear bond strength), 0.45% or 0.5% by weight of CQ, 0.76% or 0.84% by weight of EHA, and 0.002% by weight of BHT were added to the resin mixtures. All of the mixtures were stirred until they gave an optically clear solution.

TABLE 1

|  | Reference 1 | Example 1 | Example 2 | Reference 2 | Example 3 | Example 4 |
|---|---|---|---|---|---|---|
| TEDMA | 100 | 99 | 90 | 80 | 79.2 | 72 |
| E3TMPTA |  |  |  | 20 | 19.8 | 18 |
| MDP |  | 1 | 10 |  | 1 | 10 |
| CQ | 0.5 | 0.5 | 0.45 | 0.5 | 0.5 | 0.45 |
| EHA | 0.84 | 0.84 | 0.76 | 0.84 | 0.84 | 0.76 |
| BHT | 0.002 | 0.002 | 0.002 | 0.002 | 0.002 | 0.002 |
| Viscosity [mPas] | 10 | 8 | 11.9 | 12 | 12.0 | 17.0 |
| Surface tension [mN/m] | 35.07 | 35.37 | 35.12 | 35.37 | 35.96 | 35.63 |
| Contact angle enamel [°] | 0.4 | 0.8 | 1.7 | 2.4 | 1.0 | 2.1 |
| Penetration coefficient [cm/s] | 175 | 221 | 148 | 147 | 150 | 105 |
| TCD [mm] after 20 s exposure | 0 | 10 | 10 | 4.1 | 10 | 10 |
| TCD [mm] after 15 s exposure | 0 | 6.4 | 7.5 | 3.5 | 8.04 | 9.5 |
| SBS measurements [MPa] on unetched bovine enamel; average (SD); number of individual measurements | 3.8 (0.8) n = 8 | 10.1 (1.8) n = 8 |  |  | 12.1 (1.6) n = 7 | 14.7 (1.9) n = 6 |
| SBS measurements [MPa] on HCl-etched, bovine enamel; average (SD); number of individual measurements | 21.0 (1.4) n = 8 | 22.7 (2.4) n = 7 |  |  | 24.8 (2.3) n = 8 | 26.5 (4.1) n = 6 |

The composition in Table 1 is indicated in parts by weight.

Table 1 shows that the addition even of small amounts of the acidic monomer MDP leads to a significantly improved through-cured depth. The combination of the addition of an acidic monomer MDP and of a crosslinking monomer having three polymerizable groups (E3TMPTA) leads to excellent through-cured depths even with a low exposure time.

Furthermore, table 1 shows that the inventive examples exhibit improved adhesion to HCl-etched bovine enamel. A particular advantage is the drastically improved adhesion to unetched bovine enamel.

Reference 3 and example 5 (table 2) were produced by adding 5 parts and 30 parts, respectively, of MDP to a mixture of 80 parts of TEDMA, 20 parts of E3TMPTA, 0.64 part of CQ, 1.06 part of EHA, and 0.003 part of BHT. The mixtures were protected from light or were exposed only to yellow light; all the measurements were carried out under corresponding conditions in order to rule out unwanted polymerization of the mixture.

TABLE 2

|  | Reference 3 | Example 5 |
|---|---|---|
| TEDMA | 55.1 | 74.7 |
| E3TMPTA | 13.8 | 18.7 |
| MDP | 30 | 5 |
| CQ | 0.44 | 0.59 |
| EHA | 0.73 | 1.00 |
| BHT | 0.002 | 0.002 |
| Viscosity [mPas] | 38 | 12 |
| Penetration coefficient [cm/s] | 46 | 146 |
| Water absorption [µg/mm³] | 103.1 (3.2) | 68.0 (1.7) |
| Solubility [µg/mm³] | 14.1 (1.0) | 2.3 (0.5) |
| TCD [mm]         10 s | 8.2 | 3.3 |
| 15 s | 9.9 | 5.2 |
| Color difference (ΔE) | 3.0 (1.0); n = 9 | 14.9 (5.0); n = 7 |
| SBS [MPa] unetched |  |  |

The compositions are indicated in parts by weight (rounded).

In spite of a relatively low initiator fraction, reference 3 showed an increase in through-cured depth (TCD) after 10 s. The high fraction of MDP resulted in a penetration coefficient of less than 50 cm/s. The bond strength (SBS) was only 3 MPa. Reference 3 also exhibited water absorption, water solubility and/or color stability which was such as to make the composition disadvantageous for use in accordance with the invention. The water absorption and water solubility of the composition without addition of MDP, which were likewise measured for purposes of comparison, were 60.8(2.7) and 1.5 µg/mm³, respectively. The water absorption and water solubility were determined in accordance with ISO 4049:2000, the specimens made from the stated resins being cured by 2×180 s exposure in a photopolymerization apparatus (Heraflash).

The color stability was determined by curing specimens made from the stated resins by 2×180 s exposure in a photopolymerization apparatus (Heraflash) in accordance with ISO 4049:2000 (color stability) and then storing them in demineralized water in the dark at 60° C. At the start and after defined intervals of time, the color of the specimens was measured using an electronic colorimeter in accordance with a CIE standard. The color differences (deviations in the L, a, b values) of the specimens are reported in ΔE units. The greater the ΔE value, the greater the color change of the specimen.

The invention claimed is:

1. An infiltrant for dental application comprising crosslinking monomers, said infiltrant comprising 0.05%-20% by weight of acid-group-containing monomers, 20% by weight or less of solvent, and less than 5% by weight of water, and having a dynamic viscosity at 23° C. of 50 mPas or less.

2. A method of treating carious enamel lesions, comprising:

i) removing a thin surface layer of a enamel lesion using an etching agent;
ii) rinsing to remove said etching agent from said lesion;
iii) drying said lesion with a drying agent;
iv) infiltrating said lesion with an infiltrant comprising crosslinking monomers, said infiltrant comprising 0.05%-20% by weight of acid-group-containing monomers and 20% by weight or less of solvent, and having a dynamic viscosity at 23° C. of 50 mPas or less; and
v) curing the infiltrant in said lesion.

3. The method of claim 2, wherein said infiltrant has a dynamic viscosity at 23° C. of 30 mPas or less.

4. The method of claim 2, wherein said infiltrant has a dynamic viscosity at 23° C. of 20 mPas or less.

5. The method of claim 2, wherein said infiltrant comprises less than 5% by weight of water.

6. The method of claim 2, wherein said infiltrant comprises less than 2% by weight of water.

7. The method of claim 2, wherein said infiltrant contains 10%, by weight or less of solvent.

8. The method of claim 2, wherein said infiltrant contains essentially no solvent.

9. The method of claim 2, wherein said infiltrant has a penetration coefficient PC>50 cm/s.

10. The method of claim 2, wherein said infiltrant has a penetration coefficient PC>100 cm/s.

11. The method of claim 2, wherein said infiltrant further comprises monomers having one polymerizable group.

12. The method of claim 2, wherein said infiltrant comprises crosslinking monomers having two polymerizable groups, wherein said two polymerizable groups are esters of acrylic or methacrylic acid.

13. The method of claim 2, wherein the amount of acid-group-containing monomers is 0.1% to 15%, of the infiltrant, by weight.

14. The method of claim 2, wherein the acid-group-containing monomers contain phosphoric and/or phosphonic acid groups.

15. The method of claim 2, wherein the acid-group-containing monomers contain one or two polymerizable group(s).

16. The method of claim 2, wherein the acid-group-containing monomers are acrylates, methacrylates, acrylamides and/or methylacrylamides.

17. The method of claim 2, wherein the amount of acid-group-containing monomers is 0.2% to 10%, of the infiltrant, by weight.

18. The method of claim 2, wherein the amount of acid-group-containing monomers is 0.5% to 5%, of the infiltrant, by weight.

19. The method of claim 2, wherein the amount of acid-group-containing monomers is 0.5% to 2%, of the infiltrant, by weight.

20. The method of claim 7, wherein the acid-group-containing monomers contain one polymerizable group.

21. The method of claim 12, wherein the fraction of crosslinking monomers having two polymerizable groups is 99.8% to 50%, of the infiltrant, by weight.

22. The method of claim 12, wherein the fraction of crosslinking monomers having two polymerizable groups is 99.5% to 60%, of the infiltrant, by weight.

23. The method of claim 12, wherein the fraction of crosslinking monomers having two polymerizable groups is 99% to 60%, of the infiltrant, by weight.

24. The method of claim 12, wherein the fraction of crosslinking monomers having two polymerizable groups is 99% to 70%, of the infiltrant, by weight.

25. The method of claim 12, wherein said esters of acrylic or methacrylic acid are selected from the group consisting of allyl methacrylate; allyl acrylate; PRDMA, 1,3-propanediol dimethacrylate; BDMA, 1,3-butanediol dimethacrylate; BDDMA, 1,4-butanediol dimethacrylate; PDDMA, 1,5-pentanediol dimethacrylate, NPGDMA, neopentyl glycol dimethacrylate; HDDMA, 1,6-hexanediol dimethacrylate; NDDMA, 1,9-nonanediol dimethacrylate; DDDMA, 1,10-decanediol dimethacrylate; DDDDMA, 1,12-dodecanediol dimethacrylate; PRDA, 1,3-propanediol diacrylate; BDA, 1,3-butanediol diacrylate; BDDA, 1,4-butanediol diacrylate; PDDA, 1,5-pentanediol diacrylate; NPGDA, neopentyl glycol diacrylate; HDDA, 1,6-hexanediol diacrylate; NDDA, 1,9-nonanediol diacrylate; DDDA, 1,10-decanediol diacrylate; DDDDA, 1,12-dodecanediol dimethacrylate; EGDMA, ethylene glycol dimethacrylate; DEGDMA, diethylene glycol dimethacrylate; TEDMA, triethylene glycol dimethacrylate; TEGDMA, tetraethylene glycol dimethacrylate; EGDA, ethylene glycol diacrylate; DEGDA, diethylene glycol diacrylate; TEDA, triethylene glycol diacrylate; TEGDA, tetraethylene glycol diacrylate; PEG200DMA, polyethylene glycol 200 dimethacrylate; PEG300DMA, polyethylene glycol 300 dimethacrylate; PEG400DMA, polyethylene glycol 400 dimethacrylate; PEG600DMA, polyethylene glycol 600 dimethacrylate; PEG200DA, polyethylene glycol 200 diacrylate; PEG300DA, polyethylene glycol 300 diacrylate; PEG400DA, polyethylene glycol 400 diacrylate; PEG600DA, polyethylene glycol 600 diacrylate; PPGDMA, polypropylene glycol dimethacrylate; PPGDA, polypropylene glycol diacrylate; NPG (PO) 2DMA, propoxylated (2) neopentyl glycol dimethacrylate; NPG (PO) 2DA, propoxylated (2) neopentyl glycol diacrylate; bis-MA, bisphenol A dimethacrylate; bis-GMA, bisphenol A glycerol dimethacrylate; BPA (EO) DMA, ethoxylated bisphenol A dimethacrylate (EO=1-30); BPA (PO) DMA, propoxylated bisphenol A dimethacrylate (PO=1-30); BPA (EO) DA, ethoxylated bisphenol A diacrylate (EO=1-30); BPA (PO) DA, propoxylated bisphenol A diacrylate (PO=1-30); BPA (PO) GDA, propoxylated bisphenol A glycerol diacrylate; UDMA, diurethane dimethacrylate; TCDDMA, tricyclo[5.2.1.0]decanedimethanol dimethacrylates; TCDDA, tricyclo[5.2.1.0]decanedimethanol diacrylates; EBA, N,N'-ethylenebisacrylamide; DHEBA, N,N'-(1,2-dihydroxyethylene)bisacrylamide; DEPBA, N,N'-diethyl(1,3-propylene)bisacrylamide; TMHMBMA, N,N'-(2,2,4-trimethylhexamethylene)bismethacrylamide; and bis[2-(2-methylacrylamino)ethoxycarbonyl]hexamethylenediamine.

26. The method of claim 2, wherein said infiltrant comprises crosslinking monomers having at least three polymerizable groups.

27. The method of claim 26, wherein 0% to 50% of said crosslinking monomers have at least three polymerizable groups.

28. The method of claim 26, wherein the crosslinking monomers having at least three polymerizable groups have the formula below

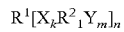

having the following definitions:
$R^1$ is a linear or branched hydrocarbon having 3-24 C atoms, comprising alkyl, cycloalkyl or aryl;
$R^2$ is a linear or branched hydrocarbon having 1-16 C atoms, comprising alkyl, cycloalkyl or aryl;
X is a linking group identically or differently selected from an ether group, carbonyl group, ester group, amide group, urethane group or urea group;

Y is a group identically or differently containing a polymerizable double bond and/or a ring-openingly polymerizable group and/or a thiol group and/or an epoxide group and/or a vinyl, preferably (meth)acrylate and/or (meth)acrylamide;

k is 0 or 1;
l is 0 or 1;
m is a least 1;
n is at least 1; and
m×n is at least 3.

29. The infiltrant of claim 26, wherein the crosslinking monomers having at least three polymerizable groups are selected from the group consisting of TMPTMA, trimethylolpropane trimethacrylate; TMPTA, trimethylolpropane triacrylate; DTMPTA, ditrimethylolpropane tetra(meth)acrylate; diPENTA, dipentaerythritol penta(meth)acrylate; GPTA, propoxylated glyceryl tri(meth)acrylate; DPEHA, dipentaerythritol hexa(meth)acrylate; and ethoxylated trimethylolpropane tri(meth)acrylate.

30. The method of claim 26, wherein the fraction of crosslinking monomers having at least three polymerizable groups is 10% to 50%, of the infiltrant, by weight.

31. The method of claim 26, wherein the fraction of crosslinking monomers having at least three polymerizable groups is 10% to 30%, of the infiltrant, by weight.

32. The method of claim 26, wherein the crosslinking monomers having at least three polymerizable groups have a distance between crosslinking points of at least 7 bond lengths.

33. The method of claim 26, wherein the crosslinking monomers having at least three polymerizable groups have a distance between crosslinking points of not more than 50 bond lengths.

34. The method of claim 26, wherein the crosslinking monomers having at least three polymerizable groups have a distance between crosslinking points of 11 to 21 bond lengths.

35. The method of claim 26, wherein the fraction of crosslinking monomers having at least three polymerizable groups and a distance between crosslinking points of less than 10 bond lengths, based on the total mass of the monomers is less than 20% by weight.

36. The method of claim 25, wherein the fraction of crosslinking monomers having at least three polymerizable groups and a distance between crosslinking points of less than 10 bond lengths, based on the total mass of the monomers is less than 10% by weight.

37. The method of claim 25, wherein the fraction of crosslinking monomers having at least three polymerizable groups and a distance between crosslinking points of less than 10 bond lengths, based on the total mass of the monomers is less than 5% by weight.

38. The method of claim 28, wherein $R^1$ contains O, N, Si, S, and/or P as heteroatoms.

39. The method of claim 28, wherein $R^1$ comprises one or more of siloxane, cyclosiloxane, carbosilane, cyclocarbosilane, an ether group, a polyether group, a polyester group, a polysiloxane group and/or a polycarbosilane group.

40. The method of claim 28, wherein $R^1$ is substituted by one or more of an hydroxyl, a carbonyl, a halogen, an ammonium-alkylene groups, a siloxane, a cyclosiloxane, a carbosilane and/or a cyclocarbosilane.

41. The method of claim 40, wherein said halogen is fluorine.

42. The method of claim 28, wherein $R^2$ contains O, N, Si, S, and/or P as heteroatoms.

43. The method of claim 28, wherein $R^2$ comprises one or more of siloxane, cyclosiloxane, carbosilane, cyclocarbosilane, an ether group, a polyether group, a polyester group, a polysiloxane group and/or a polycarbosilane group.

44. The method of claim 28, wherein $R^2$ is substituted by one or more of an hydroxyl, a carbonyl, a halogen, an ammonium-alkylene groups, a siloxane, a cyclosiloxane, a carbosilane and/or a cyclocarbosilane.

45. The method of claim 44, wherein said halogen is fluorine.

46. The method of claim 26, wherein the crosslinking monomers having at least three polymerizable groups are selected from the group consisting of propoxylated glyceryl tri(meth)acrylate; ethoxylated trimethylolpropane trimethacrylate, ethoxylated trimethylolpropane triacrylate, propoxylated trimethylolpropane trimethacrylate, propoxylated trimethylolpropane triacrylate, ethoxylated pentaerythritol trimethacrylate, ethoxylated pentaerythritol triacrylate, ethoxylated pentaerythritol tetramethacrylate, ethoxylated pentaerythritol tetraacrylate, ethoxylated dipentaerythritol trimethacrylate, ethoxylated dipentaerythritol tetramethacrylate, ethoxylated dipentaerythritol pentamethacrylate, ethoxylated dipentaerythritol hexamethacrylate, ethoxylated dipentaerythritol triacrylate, ethoxylated dipentaerythritol tetraacrylate, ethoxylated dipentaerythritol pentaacrylate, ethoxylated dipentaerythritol hexaacrylate, propoxylated pentaerythritol trimethacrylate, propoxylated pentaerythritol triacrylate, propoxylated pentaerythritol tetramethacrylate, propoxylated pentaerythritol tetraacrylate, propoxylated dipentaerythritol trimethacrylate, propoxylated dipentaerythritol tetramethacrylate, propoxylated dipentaerythritol pentamethacrylate, propoxylated dipentaerythritol hexamethacrylate, propoxylated dipentaerythritol triacrylate, propoxylated dipentaerythritol tetraacrylate, propoxylated dipentaerythritol pentaacrylate and propoxylated dipentaerythritol hexaacrylate.

47. The method of claim 2, wherein said etching agent is a gel of a strong acid.

48. The method of claim 47, wherein said strong acid is hydrochloric acid.

49. The method of claim 2, wherein said drying agent is a non-toxic solvent with a vapor pressure greater than 23 mbar at 20° C., selected from the group consisting of alcohols, ketones, ethers and esters.

50. The method of claim 49, wherein said drying agent comprises ethanol.

51. The method of claim 49, wherein said drying agent comprises a film-former.

52. A kit comprising:
   i) an etching agent
   ii) a drying agent; and
   iii) an infiltrant comprising crosslinking monomers, said infiltrant comprising 0.05% to 20% by weight of acid-group-containing monomers and 20% by weight or less of solvent, and having a dynamic viscosity at 23° C. of 50 mPas or less.

53. The kit of claim 52, wherein said etching agent is a gel of a strong acid.

54. The kit of claim 53, wherein said strong acid is hydrochloric acid.

55. The kit of claim 52, wherein said drying agent is a non-toxic solvent with a vapor pressure greater than 23 mbar at 20° C., selected from the group consisting of alcohols, ketones, ethers and esters.

56. The kit of claim 55, wherein said drying agent comprises ethanol.

57. The kit of claim 52, wherein said drying agent comprises a film-former.

\* \* \* \* \*